United States Patent [19]

Kleintjens et al.

[11] Patent Number: 4,547,587

[45] Date of Patent: Oct. 15, 1985

[54] PROCESS FOR THE PREPARATION OF PHARMACEUTICAL BENZOIC ACID

[75] Inventors: Ludovicus A. L. Kleintjens, Stein; Hubertus M. J. Grooten, Simpelveld, both of Netherlands

[73] Assignee: Stamicarbon B.V., Geleen, Netherlands

[21] Appl. No.: 564,199

[22] Filed: Dec. 22, 1983

[30] Foreign Application Priority Data

Jan. 3, 1983 [NL] Netherlands ......................... 8300009

[51] Int. Cl.$^4$ ............................................. C07C 51/42
[52] U.S. Cl. .................................... 562/494; 562/412; 562/415
[58] Field of Search ..................... 562/412, 415, 494

[56] References Cited

U.S. PATENT DOCUMENTS

| | | | |
|---|---|---|---|
| 1,380,277 | 5/1921 | Weiss et al. | 562/415 |
| 1,686,913 | 10/1927 | Jaeger | 562/494 |
| 1,851,361 | 3/1932 | Jaeger et al. | 562/415 |

*Primary Examiner*—Paul J. Killos
*Attorney, Agent, or Firm*—Cushman, Darby & Cushman

[57] ABSTRACT

Pharmaceutical benzoic acid is prepared from raw benzoic acid made of oxidation of toluene with an oxygen containing gas, the process is characterized in that the oxidation reaction product is contacted with at least 1 m$^3$ per kg of benzoic acid of a gas with a critical temperature lower than 435 K by passing this gas through the oxidation reaction product at a flow rate of at least 1 m$^3$ per hour per kg of benzoic acid at a temperature of 340–600 K. and a pressure of at least 3 MPa. The pharmaceutical benzoic acid is separated from the mixture by cooling it to 315–370 K. at a pressure of 3–300 MPa.

11 Claims, No Drawings

PROCESS FOR THE PREPARATION OF PHARMACEUTICAL BENZOIC ACID

The invention relates to a process for the preparation of pharmaceutical benzoic acid, which means the benzoic acid is to meet the specifications of USP 20, according to which raw benzoic acid is prepared by oxidation of toluene with gas containing molecular oxygen.

This oxidation may take place both in the gas phase and in the liquid phase.

In the gas-phase oxidation of toluene to benzoic acid it is preferred to apply temperatures of 450–750 K. and pressures of 50–2000 kPa. Such a process for the preparation of benzoic acid by gas-phase oxidation of toluene is known from European patent application laid open for public inspection No. 40452.

In the liquid-phase oxidation of toluene to benzoic acid by preference temperatures of 390–500 K. and pressures of 200–2000 kPa are applied. This liquid-phase oxidation may take place in the presence of a solvent, for instance an aliphatic carboxylic acid, in particular acetic acid, and/or in the presence of a halogen-containing substance acting as promotor, but in view of corrosion problems this oxidation by preference takes place in the absence of an aliphatic carboxylic acid and in the absence of a halogen-containing substance acting as promotor. Such a process for the preparation of benzoic acid by liquid-phase oxidation of toluene is known from U.S. Pat. No. 4.339.599.

A major drawback of these known methods for the preparation of benzoic acid is that the raw benzoic acid formed in the oxidation contains a rather large amount of impurities, and with the methods currently known for this it is difficult to reduce at least a substantial portion of these impurities to the very low concentrations specified for pharmaceutical benzoic acid.

The object of the invention is to provide a simple process for the preparation of pharmaceutical benzoic acid.

The invention therefore relates to a process for the preparation of pharmaceutical benzoic acid starting from raw benzoic acid prepared by oxidation of toluene with gas containing molecular oxygen, which process is characterized in that the oxidation reaction product formed is contacted, in a liquid form or in finely distributed solid form, with at least 1 m$^3$ (NTP) per kg benzoic acid of a gas or gas mixture of which the critical temperature is lower than 435 K., such as $SO_2$, $N_2O$, $NO_2$, NO, CO, $CH_4$, $N_2$, $CO_2$ and ethylene and those mixtures, of these gases among themselves and/or with less than 50 vol. % of other gases, of which the critical temperature is lower than 435 K., $CO_2$, ethylene or mixtures of these two gases being preferred, the contact being established by leading this gas or gas mixture through the oxidation reaction product, preferably during 1–100 minutes and in particular during 5–75 minutes, the flow rate being at least 1 m$^3$ (NTP) and preferably 10–500 m$^3$ (NTP) of gas per hour per kg benzoic acid, at a temperature of 340–600 K. and preferably 360–500 K. and in particular 370–450 K. and a pressure of at least 3 MPa and preferably below 300 MPa and in particular 5–100 MPa, and subsequently the pharmaceutical benzoic acid is separated from this gas loaded with benzoic acid and impurities by cooling said gas to 315–370 K. and preferably to 320–350 K. at a pressure of 3–300 MPa and in particular at a pressure of 5–100 MPa.

The process according to the invention will be elucidated on the basis of the following, non-limiting examples. In these examples use is made of benzoic acid with an impurity content, relative to the total weight, of 0.02 wt. % diphenyl oxide (DPO), 0.02 wt. % 2-methyldiphenyl (2-MDP) and 0.16 wt. % of 3-methyldiphenyl and 4-methyldiphenyl combined (3- and 4-MDP).

EXAMPLE I

An amount of 5 g benzoic acid flakes was melted at 393 K. in a $CO_2$ atmosphere at 10 MPa. Subsequently, $CO_2$ was during 30 minutes passed through this liquid, the flow rate being 160 m$^3$ (NTP) gas per kg benzoic acid per hour, at 393 K. and 9.5–10.5 MPa. The gas loaded with benzoic acid was cooled to 328 K. at 9.5–10.5 MPa, upon which benzoic acid crystals separated off.

The benzoic acid crystals thus obtained were subsequently analysed. The analysis showed that, relative to the total weight, the purified benzoic acid still had a 3- and 4-MDP content of only 0.00003 wt. %, while the other impurities, including the DPO, were no longer detectably present. The purified benzoic acid met the specifications of USP 20.

EXAMPLE II

An amount of 22 g benzoic acid flakes was melted at 393 K. in a $CO_2$ atmosphere at 10 MPa. Subsequently, $CO_2$ was during 30 minutes passed through this liquid, the flow rate being 30 m$^3$ (NTP) gas per kg benzoic acid per hour, at 393 K. and 9.5–10.5 MPa. The benzoic acid-loaded gas was cooled to 328 K. at 9.5–10.5 MPa, upon which benzoic acid crystals separated off.

The benzoic acid crystals thus obtained were subsequently analysed. This analysis showed that, relative to its total weight, the purified benzoic acid still contained only 0.008 wt. % 3- and 4-MDP, while the other impurities, including the DPO, were no longer detectably present. The purified benzoic acid met the specifications of USP 20.

EXAMPLE III

An amount of 10 g benzoic acid flakes was melted at 400 K. in a $CO_2$ atmosphere at 10 MPa. Subsequently, $CO_2$ was during 60 minutes passed through this liquid, the flow rate being 50 m$^3$ (NTP) gas per kg benzoic acid per hour, at 400 K. and 9.5–10.5 MPa. The benzoic acid-loaded gas was cooled to 328 K. at 9.5–10.5 MPa, upon which benzoic acid crystals separated off.

The benzoic acid crystals thus obtained were subsequently analysed. The analysis showed that, relative to its total weight, the purified benzoic acid still had a total content of impurities of only 0.004 wt. %. The purified benzoic acid met the specifications of USP 20.

EXAMPLE IV

An amount of 12 g benzoic acid flakes was melted at 393 K. in an ethylene atmosphere at 10 MPa. Subsequently, ethylene was during 30 minutes passed through this liquid, the flow rate being 167 m$^3$ (NTP) gas per kg benzoic acid per hour at 393 K. and 9.5–10.5 MPa. The gas loaded with benzoic acid was cooled to 320 K. at 9.5–10.5 MPa, upon which benzoic acid crystals separated off.

The benzoic acid crystals thus obtained were subsequently analysed. The analysis showed that no detectable amounts of impurities were still present in the purified benzoic acid. The purified benzoic acid met the specifications of USP 20.

EXAMPLE V

An amount of 5 g benzoic acid flakes was melted at 393 K. in an ethylene atmosphere at 10 MPa. Subsequently, ethylene was during 30 minutes passed through this liquid, the flow rate being 200 m$^3$ (NTP) gas per kg benzoic acid per hour, at 393 K. and 9.5–10.5 MPa. The gas loaded with benzoic acid was cooled to 320 K. at 9.5–10.5 MPa, upon which benzoic acid crystals separated off.

The benzoic acid crystals thus obtained were subsequently analysed. The analysis showed that no detectable amounts of contaminants were still present in the purified benzoic acid. The purified benzoic acid met the specifications of USP 20.

We claim:

1. In a process for the preparation of pharmaceutical benzoic acid by the oxidation of toluene in the presence of a molecular oxygen containing gas yielding a reaction product containing impurities, the improvement essentially comprising purifying said reaction product in liquid or finely divided solid form by contacting it with a gas phase essentially consisting of at least one gas having a critical temperature lower than 435 K., by passing said gas phase, in an amount of at least 1 m$^3$ (NTP) per kg benzoic acid, through said reaction product at a flow rate of at least 1 m$^3$ (NTP) gas per hour per kg benzoic acid, at a temperature within the range of between about 340 and 600 K. and at a pressure of at least 3 MPa, whereby at least a portion of said reaction product with impurities is taken into said gas phase, and subsequently selectively separating pharmaceutical benzoic acid from said gas phase by cooling said gas phase to a temperature of between about 315 and 370 K. at a pressure of between about 3 and 300 MPa.

2. The process of claim 1 wherein said gas phase is selected from the group consisting of $CO_2$, ethylene, and a mixture thereof.

3. The process of claim 1 wherein said gas phase is passed through said reaction product over a period of between about 1 and 100 minutes.

4. The process of claim 3 wherein said gas phase is passed through said reaction product over a period of between about 5 and 75 minutes.

5. The process of claim 1 wherein said gas flow rate is between about 10 and 500 m$^3$ (NTP) gas per hour per kg benzoic acid.

6. The process of claim 1 wherein said gas phase is passed through said reaction product at a temperature of between about 360 and 500 K.

7. The process of claim 6 wherein said gas phase is passed through said reaction product at a temperature of between about 370 and 450 K.

8. The process of claim 1 wherein said gas phase is passed through said reaction product at a pressure of between about 3 and 300 MPa.

9. The process of claim 8 wherein said gas phase is passed through said reaction product at a pressure of between about 5 and 100 MPa.

10. The process of claim 1 wherein said gas phase, after having taken up said reaction product with impurities, is cooled to a temperature of between about 320 and 350 K.

11. The process of claim 1 wherein said pharmaceutical benzoic acid is selectively separated from said gas phase at a pressure of between about 5 and 100 MPa.

* * * * *